United States Patent [19]

Berke et al.

[11] Patent Number: 5,100,621
[45] Date of Patent: Mar. 31, 1992

[54] TEST KIT FOR DIAGNOSTIC PROCEDURES

[75] Inventors: Carl M. Berke, Boston; Thomas L. Collins, Springfield; David P. Leja, Belchertown; Ronald W. Mink, Wilbraham, all of Mass.

[73] Assignee: Hygeia Sciences, Inc., Newton, Mass.

[21] Appl. No.: 246,734

[22] Filed: Sep. 20, 1988

[51] Int. Cl.$^5$ .............................................. B01L 11/00
[52] U.S. Cl. .............................................. 422/61; 422/58; 422/99; 435/810; 436/808; 434/219; 434/258; 434/259; 434/428; 434/433
[58] Field of Search ............... 422/61, 99-103, 422/58; 435/810; 436/808; 434/219, 258, 259, 428-433

[56] References Cited

U.S. PATENT DOCUMENTS

| | | | |
|---|---|---|---|
| 2,370,683 | 3/1945 | Palma | 422/61 |
| 2,386,644 | 10/1945 | Williams | 434/430 |
| 2,540,432 | 2/1951 | Evans | 434/433 |
| 3,203,540 | 8/1965 | Kalt et al. | 206/12 |
| 3,272,219 | 9/1966 | Brewer | 206/12 |
| 3,743,088 | 7/1973 | Henkin | 206/12 |
| 3,786,510 | 1/1974 | Hodges | 422/61 |
| 3,917,456 | 11/1975 | Eckstein et al. | 23/254 |
| 4,056,359 | 11/1977 | Janin | 422/61 |
| 4,108,729 | 8/1978 | Mennen | 422/56 |
| 4,195,059 | 3/1980 | Whitcher et al. | 422/61 |
| 4,561,093 | 12/1985 | Doane et al. | 371/29.1 |
| 4,717,656 | 1/1988 | Swanljung | 422/58 |
| 4,877,580 | 10/1989 | Aronowitz et al. | 422/61 |
| 4,969,821 | 11/1990 | Smith | 434/433 |

Primary Examiner—Robert J. Warden
Assistant Examiner—Lyle A. Alexander
Attorney, Agent, or Firm—Staas & Halsey

[57] ABSTRACT

A test kit for performing a diagnostic procedure. The kit comprises a plastic base which has an upper surface. The base is formed from a plastic material and a plurality of upwardly opening nests are provided in the upper surface of the base. A test component is provided in each of the nests in a manner such that the components may be displayed and made available for use. The test components are preferably displayed in essentially the plane of the upper surface of the base and an instruction booklet is provided so as to overlie the test components at the beginning of the procedure. The arrangement of the components and the size and shape of the pages of the booklet are such that as the user follows the instructions and turns pages in the booklet, components remain hidden from view until needed in conducting the procedure. The pages of the booklet are progressively shorter from front to back in the booklet so that as the pages are turned components of the kit come into view as needed.

8 Claims, 3 Drawing Sheets

TEST KIT FOR DIAGNOSTIC PROCEDURES

BACKGROUND OF THE INVENTION

1. Field of the Invention

The invention of the present application relates to an improved diagnostic test kit container structure and arrangement which facilitates conduct of diagnostic procedures, particularly by untrained persons. More specifically, the kit structure and arrangement facilitates performance of the diagnostic procedures for which the kit is designed by untrained consumers in the privacy of their own homes. The kit structure and arrangement is of particular value in connection with multi-step immunoassay procedures such as are involved, for example, in the detection of strep throat.

2. Description of the Prior Art

Recently the development of highly sensitive and specific diagnostic procedures has proceeded at a rapid pace. In fields such as clinical medicine, forensic sciences, environmental quality testing, food quality assurance, drug testing and other related areas, it has become possible through use of procedures based on immunochemical reactions to determine the presence and/or amount of trace substances in test samples even when such substances are present in very low concentrations in the order of parts per million, or even less. The development of non-radioactive labels or markers, such as gold sol particles and enzyme color formers, has facilitated the use of immunoassay diagnostic procedures outside of laboratory settings and in remote sites such as physician's offices and even the homes of the users. In the physician's office, immunological procedures are useful to provide rapid, simple assays which may be performed while the patient is still in the office so that the diagnosis can be accomplished without delay and treatment instituted during a single visit. Without such simple assays, it has often been necessary for the physician to collect a sample from the patient during a first visit and to have the sample analyzed by a clinical laboratory with the results reported back to the physician by the laboratory at a later time. In the meanwhile, the patient was sent home and was required to return for a second visit with the physician in order to receive appropriate treatment and/or medication. Manifestly, such delay was inefficient and inappropriate and in some cases could even be life threatening.

Simplified testing has also become desirable to facilitate testing by the consumer in the privacy of his or her own home. The results of such testing might, for example, indicate the necessity or lack of necessity of a visit to the physician. Examples of useful tests for the "at home" market include tests for pregnancy, ovulation, streptococcus infections such as strep throat, and other infections which are detectable by analysis of urine, saliva or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling. Finally, from a commercial view point it is desirable that the test be as simple as possible requiring only minimal or no instrumentation and precluding mistakes and poor performance resulting in incorrect interpretations.

Immunoassay kits employing enzyme markers are presently commercially available for determining conditions such as pregnancy and ovulation in the physician's office and in the home of the user. The technical components generally required in such kits are (1) a solid phase bearing immobilized antibody, (2) an enzyme labelled antibody, (3) a rinse solution (in some cases this may be the users tap water), and (4) a substrate for the enzyme. A typical procedure is that the sample is mixed with a solid phase and incubated (with or without a subsequent rinse step) and then the sample is discarded, the solid phase is then contacted with the enzyme labelled antibody and incubated. Alternatively, the sample and labelled antibody may be mixed first and the mixture brought into contact with the solid phase. In either case, the solid phase may then be rinsed and contacted by the substrate for the enzyme system. After a period of time (ca 5 minutes) the color of the solid phase is observed. One such assay is described in U.S. Letters Pat. No. 4,632,901. In other known kits based on immunological reactions, gold sol particles are used as markers or labels. The gold sol particles are capable of imparting color to the reaction product without the need for a substrate.

Detection of diseases such as strep throat is more difficult because the sample generally must be collected using a swab or the like and then the antigen in the sample must be prepared for immunoassay by using an extraction procedure to free it from its chemical matrix and/or expose the reactive determinants. To this end, the sample collected on the swab may be transported and introduced into a liquid extraction medium using the swab as a stirring implement. The antigen is then contained in a liquid milieu which may be brought into contact with the immunochemical components of the test procedure.

One of the difficulties encountered in the development of test devices and kits for remote site testing is the provision of practical pre-packaged disposable kits and devices to facilitate efficient, relatively inexpensive test procedures. This, of course, requires devices and kits which are inexpensive to construct, which have a shelf life appropriate to commercial usage, which are protected against contamination during handling, and which may be simply and readily utilized when the appropriate time arises. Use in the home, in particular, also requires explicit instructions which are easy to follow and leave essentially no room for error.

A number of prior test kit structures and arrangements are illustrated in U.S. Letters Pat. Nos. 3,203,540; 3,727,391; 3,743,088; and 3,917,456. However, these kits are of limited application and do not lend themselves to home testing situations.

SUMMARY OF THE INVENTION

The present invention provides relief from many of the shortcomings of the prior art devices described above. Moreover, the test kit structure and arrangement of the present invention permits performance of sophisticated diagnostic procedures by essentially untrained persons. In this regard, the invention provides a simplified, pre-packaged disposable test kit for performing a diagnostic procedure. The kit comprises structural elements which facilitate assembly, pre-packaging and utilization of the kit components during its intended use. Thus, the kit comprises a base member having an upper surface where the kit components are displayed. Preferably, the base member includes structure defining a plurality of nests which open upwardly of the upper surface. Each of the nests may be configured for holding, displaying and presenting a test component for use by the user of the kit. In accordance with the present invention, the kit of the invention includes a test component in each of the nests presented in the upper surface and a booklet providing instructions for performing the test procedure.

The booklet of the kit of the invention has a plurality of pages and the same is initially disposed in overlying relationship across said upper surface and the components thereon. At least one page of the booklet is of a size and shape to cover the components displayed on the upper surface, and at least one additional page of the booklet is of a size and shape to expose components to be used pursuant to the instructions set forth on such additional page. The page which covers the nests and/or components is arranged to overlie and precede said additional page in said booklet.

In a more specific aspect of the invention, the upper surface of the base member is generally planar and the nests and the components therein are configured and arranged so that the components are displayed essentially in the plane of said upper surface. In a further and more specific aspect of the invention, the booklet of the test kit comprises a plurality of additional pages, such additional pages being progressively shorter from front to back in the booklet so that as the pages are turned, additional nests and components are exposed for use pursuant to instructions revealed by turning the pages.

Thus, the user simply turns the pages of the instruction booklet and as it becomes time to use a component, the necessary component is revealed while other as yet unused components remain hidden behind pages which have yet to be turned.

DETAILED DESCRIPTION OF THE INVENTION

Figure 1:
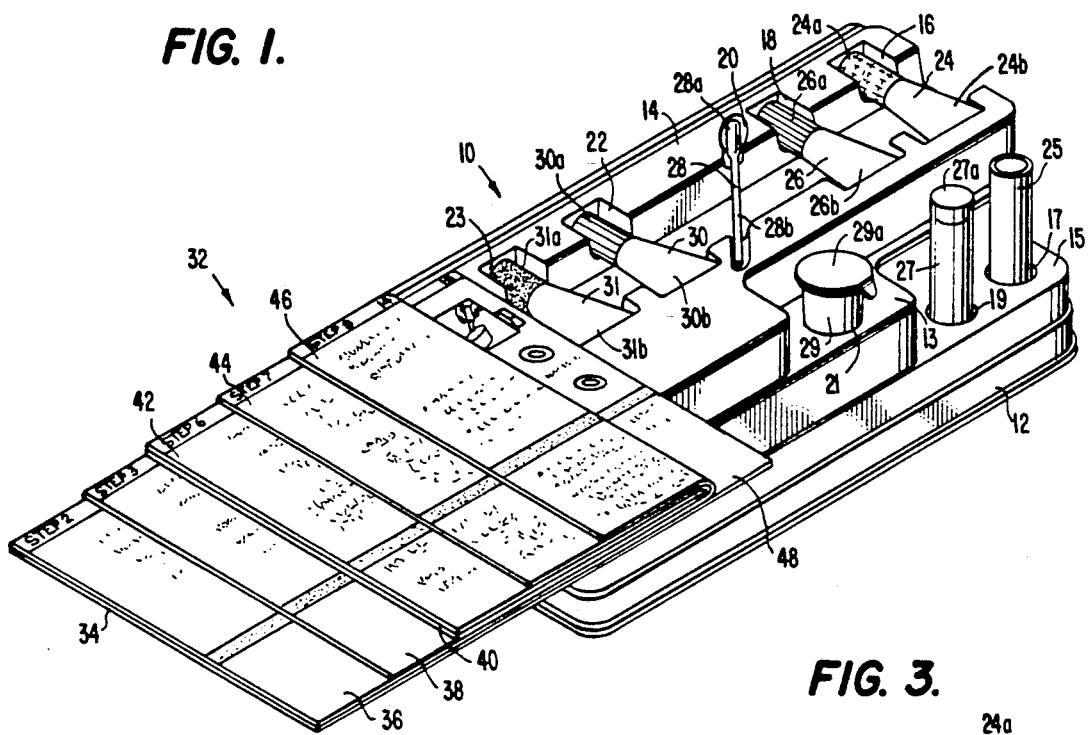
FIG. 1 is a perspective view of a test kit for performing a diagnostic procedure which embodies the principles and concepts of the invention and wherein the booklet of the kit is illustrated in its fully opened position with all of the test components exposed to open view.

A test kit 10 for performing a diagnostic procedure and which embodies the principles and concepts of the present invention is illustrated in FIG. 1, where it can be seen that the kit includes a base member 12 which has an upper surface 14. The base member 12 is preferably constructed from a thermoplastic material and may be formed utilizing conventional plastic forming methodology. The only real limitations are that the structure 12 be reasonably sturdy so as to withstand the type of handling abuse which might be encountered during normal commercial activities.

As can be seen viewing FIG. 1, member 12 includes structure presenting a number of upwardly openings nests 16 through 23, each adapted to receive, hold and display the test components 24 through 31 as illustrated in FIG. 1.

Figure 2:
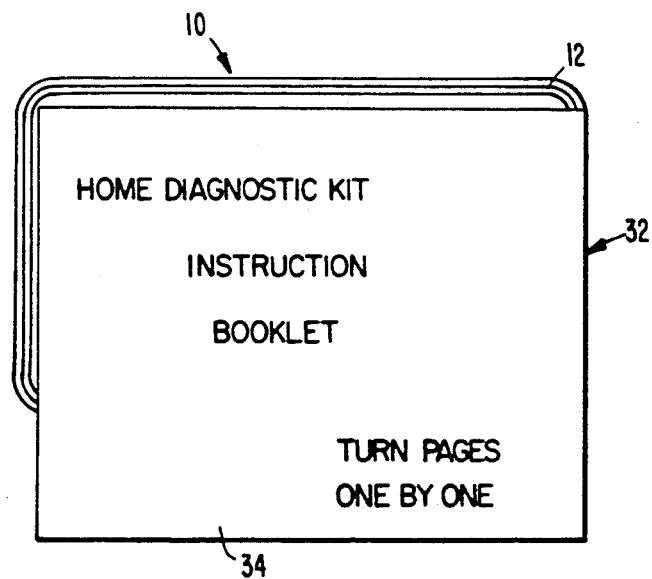
FIG. 2 is a top plan view of the kit of FIG. 1, except that the instruction booklet is illustrated in its fully closed position.

An instruction booklet 32 is illustrated in its fully opened condition in FIG. 1 and its fully closed condition in FIG. 2. It can be seen in FIG. 2 that the booklet is positioned in an overlying relationship relative to top surface 14, and when the instruction booklet 32 is completely closed, the test components are all hidden from view. Preferably, the base member 12 will include shelf structure such as the shelves 13 and 15 to accommodate larger components and facilitate presentation of all of the components of the kit in the same horizontal plane, that is in the plane of upper surface 14.

The kit of the present invention might well be utilized in connection with any one of a variety of diagnostic procedures involving an instruction booklet and a plurality of components to be utilized in accordance with a set procedure or protocol, as set forth in the instruction booklet. In this regard, the kit might be used in connection with immunoassays employing any one of a number of labels including enzymes and gold sol particles. Moreover, the kit might as well be used in connection with non-immunoassay diagnostic procedures, such as those which employ DNA probes, complex clinical chemistry and even simple chemical analysis. The important feature of the kit simply being that the user of the kit should read the instructions, and when a test component is called for in accordance with the kit protocol set forth in the booklet, such component will be in full view and available for use, while other as yet unused test components remain hidden from view. In this manner the user, and in particular an untrained user, will not be confused by having an array of unfamiliar components presented to him or her all at once.

In the preferred form of the invention illustrated in the drawings, the kit is arranged and designed to conduct a test for strep throat. And for such purposes the components of the kit are those which are required in accordance with conventional methodology for conducting such a test. In this regard, test component 24 may consist of a squeezable plastic container comprising a yellow cap 24a and tube 24b and containing a solution adapted for extracting and solubilizing streptococcal components from a throat swab and otherwise preparing the streptococcal organisms for conduct of the test procedures. Such materials and methodology are known. Moreover, as set forth above, the invention does not involve the specific immunogen to be detected or the specific methodology for making such detection. Rather, the present invention relates to the container structure and arrangement of components which facilitates conduct of diagnostic procedures and protocols generally.

As illustrated, test component 25 consists of a vial or test tube that contains a dried acidic component capable of coacting with the solution in tube 24b to extract the streptococcal antigen. Component 26 consists of another squeezable plastic container comprising a red cap 26a and squeezable tube 26b and containing a solution for conducting an immunogenic reaction between extracted streptococcal antigen and an antibody which has been labelled with an enzyme component. Component 27 comprises a second vial or test tube which contains a lyophilized material comprising an antibody which has been labelled with an enzyme component. Component 27 includes a stopper or cap 27a to insure purity and maintain the dried state of the material in vial 27.

In the preferred form of the invention illustrated in the drawings, component 28 comprises a plastic dropper device which includes a squeezable bulb 28a and a long stem 28b. Component 29 comprises a test cup which may preferably be constructed exactly as illustrated in the co-pending and co-assigned application of Lennon et al., Ser. No. 107,240, filed Oct. 29, 1987. As is fully described in said co-pending Lennon et al. application, the test cup 29 includes a flow through membrane 29b to which antibody capable of immunoreacting with streptococcal antigen has been attached. The membrane 29b is visible in FIGS. 7 and 8.

Test component 30 consists of a squeezable plastic container comprising a white cap 30a and a squeezable tube 30b and containing a rinse solution. And finally, component 31 consists of a squeezable plastic container comprising a blue cap 31a and a squeezable tube 31b and containing a chemical such as an enzymatic substrate material for developing color in connection with a test control and/or a positive test.

As can be seen from FIG. 2, booklet 32 is disposed in overlying relationship relative to the surface 14 and the test components 24 through 31 thereon, hiding the latter from view. Booklet 32 comprises a plurality of separate sheets 34, 36, 38, 40, 42, 44, 46 and 48. Sheet 34 presents pages 1 and 2 of instruction booklet 32, sheet 36 presents pages 3 and 4 of booklet 32, sheet 38 presents pages 5 and 6, sheet 40 presents pages 7 and 8, sheet 42 presents pages 9 and 10, sheet 44 presents pages 11 and 12, sheet 46 presents pages 13 and 14 and sheet 48 presents page 15. In the preferred form of the invention illustrated in the drawings, the back side of sheet 48, which is opposite page 15, may be attached to upper surface 14 by an adhesive material or the like so that the booklet 32 is permanently attached to member 12.

It should be noted, that as illustrated in the drawings, the pages of booklet 32 each have a vertical height dimension from the top of the page to the bottom of the page that is greater than the width of the surface 14. Thus, the booklet projects beyond the side of base member 12. This provides extra area for setting forth instructions in two languages in the preferred form of kit 10. However, such projection beyond the bounds of the base member 12 is not an essential feature of the invention and the pages might just as well have smaller height dimensions whereby the booklet 32 does not project laterally beyond the side of base member 12 but simply overlies the extent of surface 14.

In using the kit, the user will begin with the instruction booklet in its closed position as shown in FIG. 2. Sheet 34 of booklet 32 has the first page of the instruction booklet on its front side as shown in FIG. 2 and page 2 of the booklet is on the back side of sheet 34. In the case of the embodiment illustrated in the figures, preliminary instructions are set forth at pages 1, 2 and 3 of booklet 32, and these instructions involve preliminary procedures in the case of the test for strep throat. The user is first instructed to become familiar with the throat areas to be swabbed and an illustration of this may be included. The kit includes a swab 50 (see FIG. 4) and a tongue depressor (not illustrated). The user is instructed as to how to open a package containing the swab and the tongue depressor and is cautioned that the cotton end of the swab should not be touched or placed on any surface. The tongue depressor and the swab are then utilized in a conventional manner to hold down the subject's tongue and to swab the subject's tonsils and throat.

Figure 3:
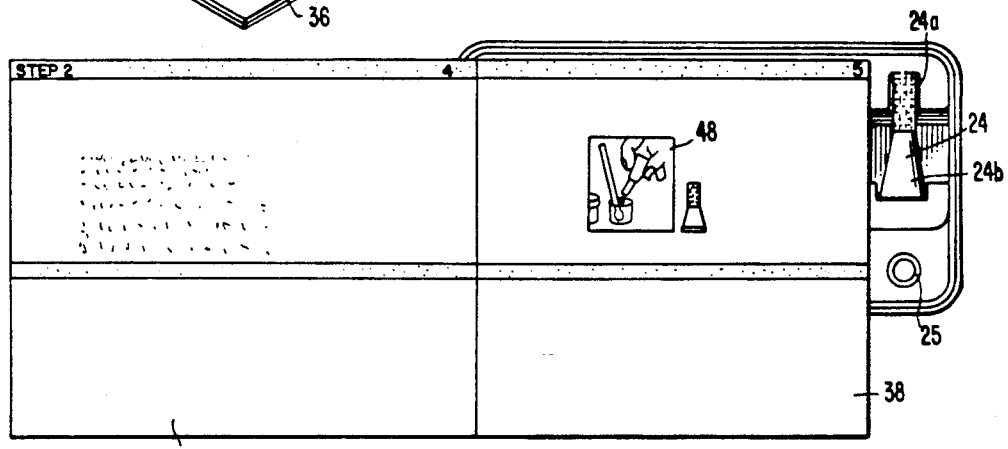
FIGS. 3, 4, 5, 6, 7 and 8 are top plan views of the kit of FIG. 1 wherein the instruction booklet is illustrated at its sequential opened positions during the use of the kit to perform a diagnostic procedure.

After swabbing has been completed in accordance with the instructions at pages 2 and 3 of the booklet, the user is instructed to proceed with step 2 which is set forth on page 4. Page 3 of the booklet comprises the front side of sheet 36, whereas page 4 of the booklet comprises the back side of sheet 36. Accordingly, to go to step 2, sheet 36 must be turned so as to open pages 4 and 5. In this regard, it is to be noted that page 5 comprises the front side of sheet 38. Upon turning to pages 4 and 5 of the booklet the kit takes the position illustrated in FIG. 3. At this point an illustration 48 may be provided to help explain the instructions, and as can be seen in FIG. 3, sheet 38 is shorter than sheet 36 so that when the latter has been turned to open pages 4 and 5, vial 25 and the squeezable plastic container 24 are exposed and displayed for use in accordance with the instructions set forth on pages 4 and 5 of the booklet.

In the present case, as has been indicated above, components 24 and 25 contain materials which act upon the streptococcal material in the swab to extract streptococcal antigen from the material in the swab and prepare the same for use in accordance with the test protocol. Thus, at page 4 on the back of sheet 36 and at page 5 on the front of sheet 38 of the booklet 32, the user is instructed to place the swab 50 in vial 25, to twist the yellow cap 24a off of the plastic tube 24b, and to squeeze the entire contents of plastic container 24 into vial 25. The user is then instructed to twirl the swab for a few seconds and to let the swab stand in the vial for a short period of time (see FIG. 4). A color change mechanism might be provided to indicate the correct operation of the step. At this stage the user is instructed to leave the swab 50 in vial 25 and to proceed to step 3 by turning sheet 38. Thus, the kit and the booklet assume the condition illustrated in FIG. 4.

Figure 4:
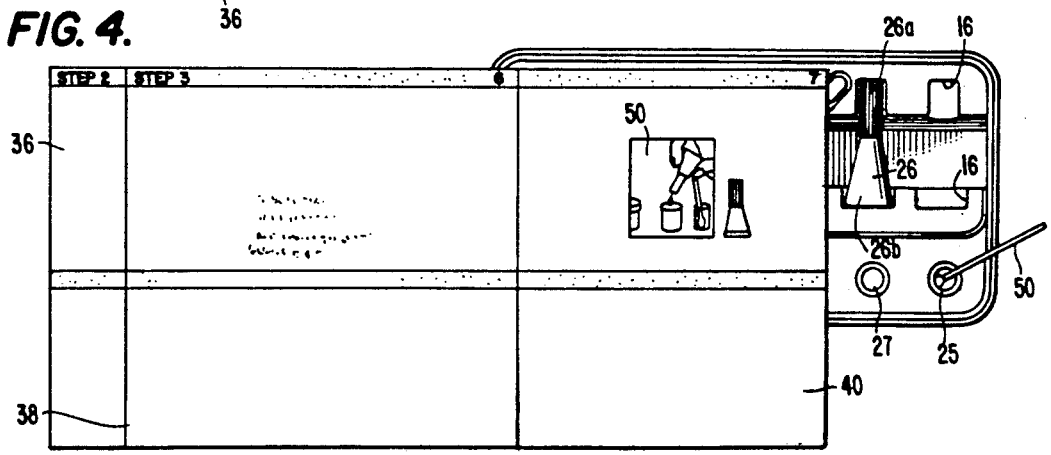

In FIG. 4, nest 16 is empty because the contents of tube 24 have been used and the tube discarded. The swab remains in vial 25. At this stage the user is instructed to remove and discard a rubber stopper 27a from test tube 27 which contains a lyophilized labelled antibody material. The user is also instructed to remove the red cap 26a from squeezable plastic tube 26b and to add all of the contents of container 26 to vial 27. These instructions are set forth on pages 6 and 7 of the booklet, page 6 comprising the back side of sheet 38 and page 7 comprising the front side of sheet 40. As indicated, another illustration 50 may be provided to assist the user. After completion of the instructions on pages 6 and 7 the user is instructed to go to the next step on page 8 of the booklet which comprises the back side of sheet 40. In this step no new materials are needed, and accordingly sheet 40 and sheet 42 may be of the same size so that no new test components are exposed. This condition is illustrated in FIG. 5.

Figure 5:
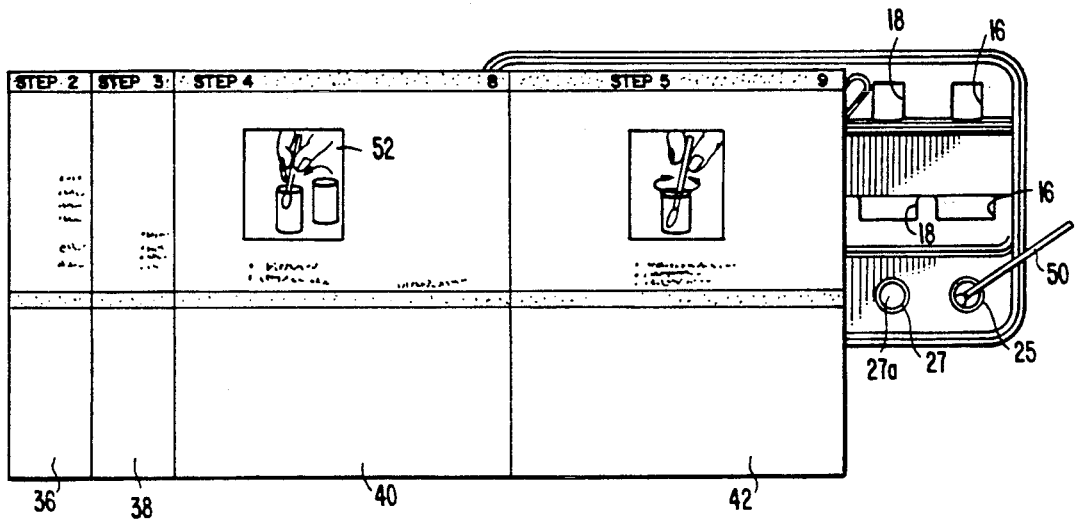

With reference to FIG. 5, nest 18 is now empty because the contents have been dispensed from container 26 and the latter has been discarded. The text on page 8 instructs the user to transfer the swab 50 from vial 25 to vial 27, to twirl the swab 50 to mix the extraction solution containing streptococcal antigen from vial 25 with the contents of vial 27 and then to allow the swab to stand in vial 27 for a short period of time. This step brings the streptococcal antigen into contact with the labelled antibody in vial 27. Again, instructions and illustrations such as the illustration 52 may be provided to guide the user.

The next step is set forth and illustrated on page 9 of the booklet which comprises the front side of sheet 42. At this stage the kit remains in the condition illustrated in FIG. 5. On page 9 the user is instructed to remove as much liquid from the swab as possible by pressing and rolling it against the inside wall of vial 25. The user is then instructed to discard the swab and to proceed to step 6 by turning sheet 42.

Figure 6:
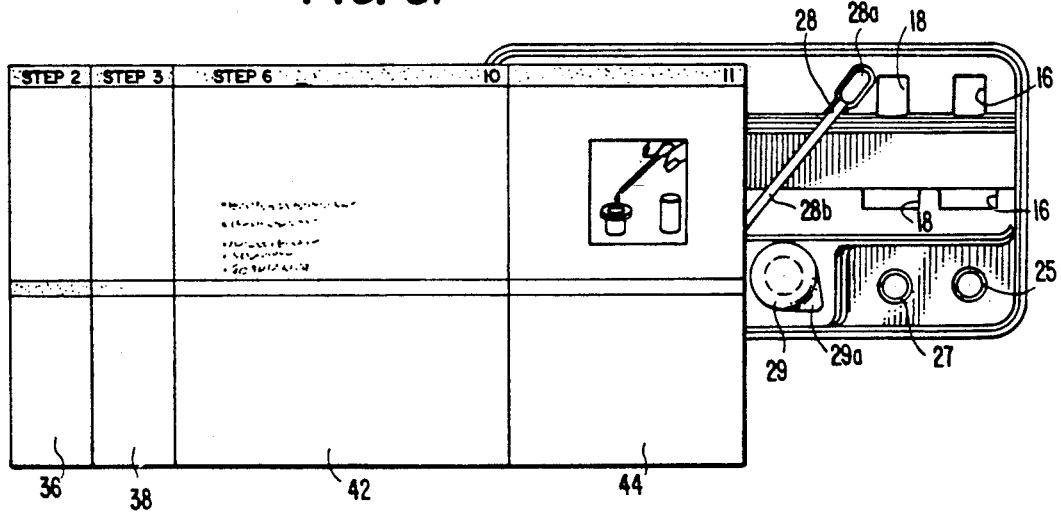

Upon turning sheet 42 of the booklet, the kit assumes the condition illustrated in FIG. 6. This exposes page 11 of the booklet which comprises the front side of sheet 44. Also, since sheet 44 is shorter than sheet 42, the turning of the latter results in the exposure of the plastic dropper 28 and the test cup 29. At pages 10 and 11 of the booklet the user is instructed to peel the foil cover 29a from the top of test cup 29 to expose membrane 29b (see FIG. 7) and to use the plastic dropper 28 to transfer 3 to 4 drops of the liquid from vial 27 onto the membrane 29b which is now exposed in the center of the opening in the top of test cup 29. The user is instructed to allow each drop to soak in to the membrane 29b. Again the instructions may include an illustration. At this stage the user is instructed to turn to the next step which appears on page 12 of the booklet on the back side of sheet 44. When sheet 44 is turned to open pages 12 and 13, the kit assumes the condition illustrated in FIG. 7.

Figure 7:
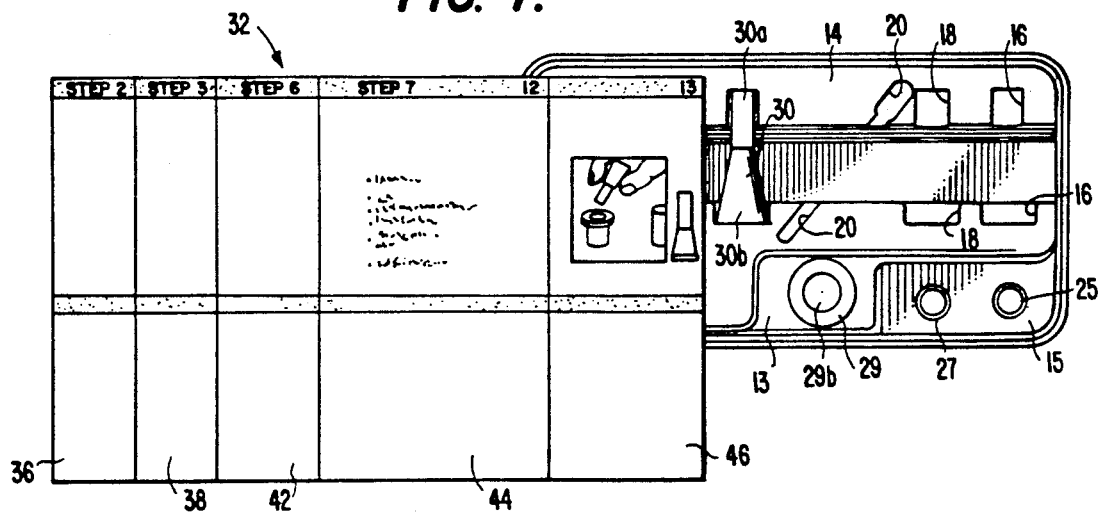

With reference to FIG. 7, sheet 46 is shorter than sheet 44 and thus the squeezable plastic container 30 is exposed and presented for utilization. On pages 12 and 13 of booklet 32, the user is instructed to remove the white cap 30a from tube 30b and to squeeze the contents of container 30 onto the membrane 29b in test cup 29. As set forth above, container 30 contains a rinse solution for rinsing non-specifically bound materials from membrane 29b and into the test cup 29. Upon completion of the steps set forth at pages 12 and 13 the user is instructed to turn sheet 46 so as to open pages 14 and 15 and expose sheet 48. The test kit now has the appearance illustrated in FIG. 8.

Figure 8:
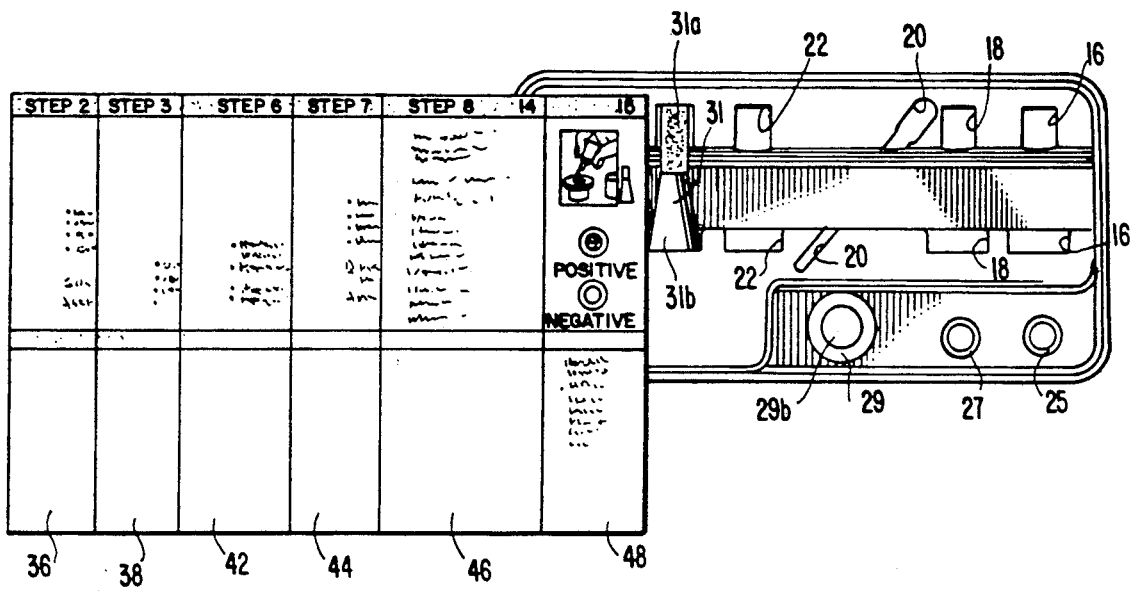

In FIG. 8 it can be seen that sheet 48 is shorter than sheet 46 and once again a new component has been revealed for utilization in accordance with the kit protocol. The instructions on page 14 on the reverse side of sheet 46 and on page 15 of the booklet on the front side of sheet 48 instruct the user to remove the blue cap 31a from squeezable tube 31b and to then squeeze the contents of container 31 into the test cup 29. The user is also instructed as to how the test results should be read. In the case of the test cup 29, the results will appear as colored configurations on the flow through membrane 29b. On these pages the user is instructed as to the meanings of the various colored configurations which may appear.

In accordance with the invention, the caps 24a, 26a, 30a and 31a may each be of a different color to further simplify the instructions and the use of the kit. In this regard, the caps and other components may be marked by color coding, numbering or lettering as desired, to facilitate identification and selection of the same in accordance with the instructions set forth in the booklet.

We claim:

1. A test kit for performing a diagnostic procedure, said kit comprising:
   a base member having an upper surface including structure for supporting, displaying and dispensing a plurality of test components;
   a plurality of test components supported and displayed on said surface, said structure defining nest being configured for displaying and dispensing on of said test components, there being a test component in each nest; and
   a booklet providing instructions for performing said procedure, said booklet having a plurality of pages and being disposed in overlying relationship across said upper surface, at least a first one of the pages of said booklet being of a size and shape to hide said test components and at least one additional page of the booklet being of a size and shape to cause components which are to be used for the first time pursuant to instructions revealed by turning said first one of the pages to be open to view, said first one of said pages overlying and preceding said additional page in said booklet.

2. A test kit as set forth in claim 1, wherein said upper surface of the base member is generally planar and said nests and the components therein are configured and arranged so that the components are displayed essentially in the plane of said upper surface.

3. A test kit as set forth in claim 1, wherein said booklet comprises a plurality of additional pages, said additional pages being progressively shorter from front to back in the booklet so that as the pages are turned, additional nests and components become exposed for use pursuant to instructions on the next unturned additional page.

4. A test kit as set forth in claim 2, wherein said booklet comprises a plurality of additional pages, said additional pages being progressively shorter from front to back in the booklet so that as the pages are turned, additional nests and components become exposed for use pursuant to instructions on the next unturned additional page.

5. A test kit as set forth in claim 1, 2, 3 or 4, wherein one or more of the test components has a mark thereon to facilitate identification thereof during use of the kit.

6. A test kit as set forth in claim 5, wherein a plurality of the test components each comprises a container containing a pourable liquid material, and each of the said containers is marked with a separate distinct marking to facilitate identification thereof.

7. A test kit as set forth in claim 5, wherein said mark is a distinct color.

8. A test kit as set forth in claim 6 wherein said separate distinct markings comprise different colors.

* * * * *

UNITED STATES PATENT AND TRADEMARK OFFICE
CERTIFICATE OF CORRECTION

PATENT NO.  : 5,100,621
DATED       : March 31, 1992
INVENTOR(S) : CARL M. BERKE, THOMAS L. COLLINS, DAVID P. LEJA and RONALD W. MINK It is certified that error appears in the above-identified patent and that said Letters Patent is hereby corrected as shown below:

Column 8, line 11, after "defining" insert --a plurality of nests which open upwardly of said surface, each--;

line 12, "on" should be --one--.

Signed and Sealed this

Twenty-second Day of June, 1993

Attest:

MICHAEL K. KIRK

Attesting Officer

Acting Commissioner of Patents and Trademarks